United States Patent [19]

Maffrand

[11] 4,161,599

[45] Jul. 17, 1979

[54] PROCESS FOR THE PREPARATION OF THIENO(2,3-c)- AND THIENO(3,2-c)PYRIDINES

[75] Inventor: Jean P. Maffrand, Toulouse, France

[73] Assignee: PARCOR, Paris, France

[21] Appl. No.: 908,857

[22] Filed: May 23, 1978

[30] Foreign Application Priority Data

Jun. 21, 1977 [FR] France .................. 77 18991

[51] Int. Cl.² .................. C09S 495/04
[52] U.S. Cl. .................. 546/114
[58] Field of Search .......... 260/294.8 C; 546/114

[56] References Cited

U.S. PATENT DOCUMENTS

| | | | |
|---|---|---|---|
| 3,969,358 | 7/1976 | Amsalem | 546/114 |
| 3,981,861 | 9/1976 | Ziemek | 546/114 |
| 3,997,545 | 12/1976 | Kuwada et al. | 546/114 |
| 4,075,340 | 2/1978 | Maffrand | 546/114 |
| 4,076,819 | 2/1978 | Maffrand | 546/114 |
| 4,097,482 | 6/1978 | Amsalem | 546/114 |

OTHER PUBLICATIONS

Farnier et al., Canadian Journal of Chemistry, vol. 54, No. 7, Apr. 1, 1976.

Primary Examiner—Alan L. Rotman
Attorney, Agent, or Firm—Young & Thompson

[57] ABSTRACT

This invention relates to a process for the preparation of derivatives having the formula:

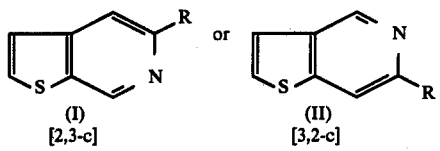

in which R is hydrogen or the carboxy group, comprising reacting a compound of the formula

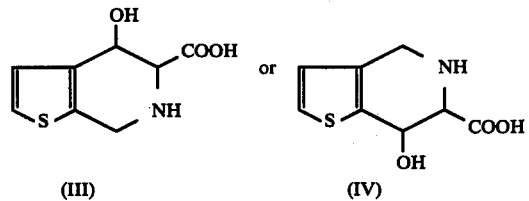

with nitrous acid, to give, respectively, the compounds of the formulae:

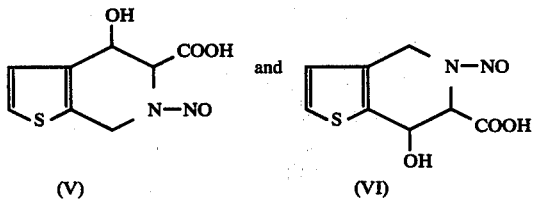

and then removing the nitroso group from the compounds of the formulae (V) and (VI), respectively, either by reaction with an acid, to give the derivatives of the formulae (I) and (II), respectively, in which R is hydrogen, or by reaction with an alkali metal hydroxide and subsequent neutralization, to give the derivatives of the formulae (I) and (II), respectively, in which R is the carboxy group.

1 Claim, No Drawings

PROCESS FOR THE PREPARATION OF THIENO(2,3-c)- AND THIENO(3,2-c)PYRIDINES

This invention relates to a new process for the preparation of thieno[2,3-c]- and thieno[3,2-c]pyridines having the formula:

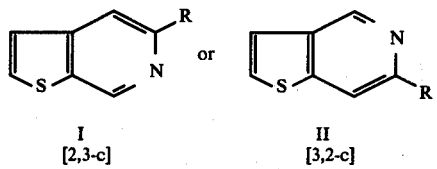

I [2,3-c]    II [3,2-c]

in which R represents hydrogen or the carboxy group. A number of methods leading to the derivatives of the formulae (I) and (II) (R=H) have been described in the literature; however, they are difficultly applicable industrially and/or too expensive. Thus, the routes mentioned by W. HERTZ & L. TSAI (J. Amer. Chem. Soc., 1963, 75, 5122), or by C. HANSCH W. CARPENTER & J. TODD (J. Org. Chem., 1958, 23, 1924), or by L. H. KLEMM, J. SHABTOY, D. R. McCOY & W. K. KRIANG (J. Het. Chem., 1968, 5883 and ibid. 1969, 6813), or by S. GRONOWITZ & E. SANDBERG (Ark. Kemi., 1970, 32, 217) exhibit the two aforementioned drawbacks.

On the other hand, the method disclosed by F. ELOY & A. DERYCKERE (Bull. Soc. Chim. Belges, 1970, 79, 301) makes use of an azide which constitutes a potential explosion hazard. Finally, the methods described by J. P. MAFFRAND & F. ELOY (J. Het. Chem., 1976, 13, 1347) and by A. HEYMES & J. P. MAFFRAND (Published French Patent Application No. 2,312,498) are more expensive than that of this invention.

The derivatives of the formulae (I) and (II) in which R=COOH were described only once in the literature, by M. FARNIER, S. SOTH & P. FOURNARI (Can. J. Chem., 1976, 54, 1067), but the process used for their preparation does not permit the production of large amounts of said materials.

The object of this invention is to provide an inexpensive process for the production, in good yields, of compounds (I) and (II) which are important intermediates in the chemical and pharmaceutical industries, particularly for the preparation of thienopyridine derivatives having various therapeutic activities, such as anti-inflammatory, anti-blood-platelet aggregation, anti-arrhythmic activities, and the like (see, for example, French patents and French published patent applications No. 2,215,948; 2,257,271; 2,315,274 and 2,345,150. Such derivatives can be produced by condensing a pyridine of compound (I) or (II) with a halide of the desired derivative-forming group to give a pyridinium salt, and then hydrogenating the pyridinium salt to give the corresponding pyridine derivative.

The process according to the present invention comprises reacting a compound of the formula

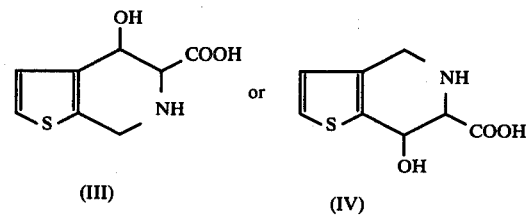

(III)    (IV)

with nitrous acid, to give compounds of the formula

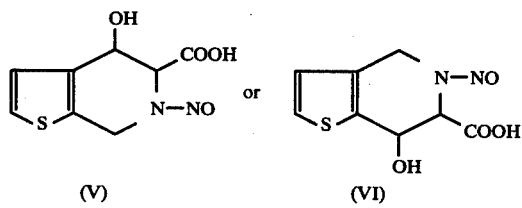

(V)    (VI)

and then removing the nitroso group of the compounds of the formula (V) or (VI) either by reaction with an acid, to give the derivatives of the formula (I) or (II) in which R is hydrogen, or by reaction with an alkali metal hydroxide and subsequent neutralization, to give the derivatives of the formula (I) or (II) in which R is the carboxy group.

Nitrous acid is preferably formed in situ, by reaction of an alkali metal nitrite (in aqueous solution) with an acid.

The reaction is typically effected by slowly adding an aqueous solution of an alkali metal nitrite, typically sodium nitrite, to a hydrochloric acid solution of the derivative of the formula (III) or (IV) maintained at 0°–15° C., and then allowing the resulting material to rest at room temperature for several hours.

Treatment of the nitrosoamine of the formula (V) or (VI) is effected with an inorganic acid such as hydrochloric acid, hydrobromic acid or sulfuric acid, preferably hydrochloric acid, or with an organic acid such as trifluoroacetic acid or trichloroacetic acid, preferably trichloroacetic acid, to give the thienopyridine of the formula (Ia) or (IIa) in which R=H.

With pure trifluoroacetic acid, the reaction is highly exothermal, whereas use of hydrochloric acid requires heating to effect the conversion.

Refluxing of the same derivatives of the formula (III) or (IV) in an aqueous alkali metal hydroxide solution, preferably in an aqueous sodium hydroxide solution, leads, after neutralization, to acids of the formula (Ib) or (IIb) (R=COOH), respectively. If desired, such acids may be decarboxylated with copper powder in the presence of quinoline, as disclosed by M. FARNIER, S. SOTH & P. FOURNARI (Can. J. Chem., 1976, 54, 1067) to give the compounds of the formula (Ia) or (IIa) (R=H).

This method may be illustrated by the following reaction scheme:

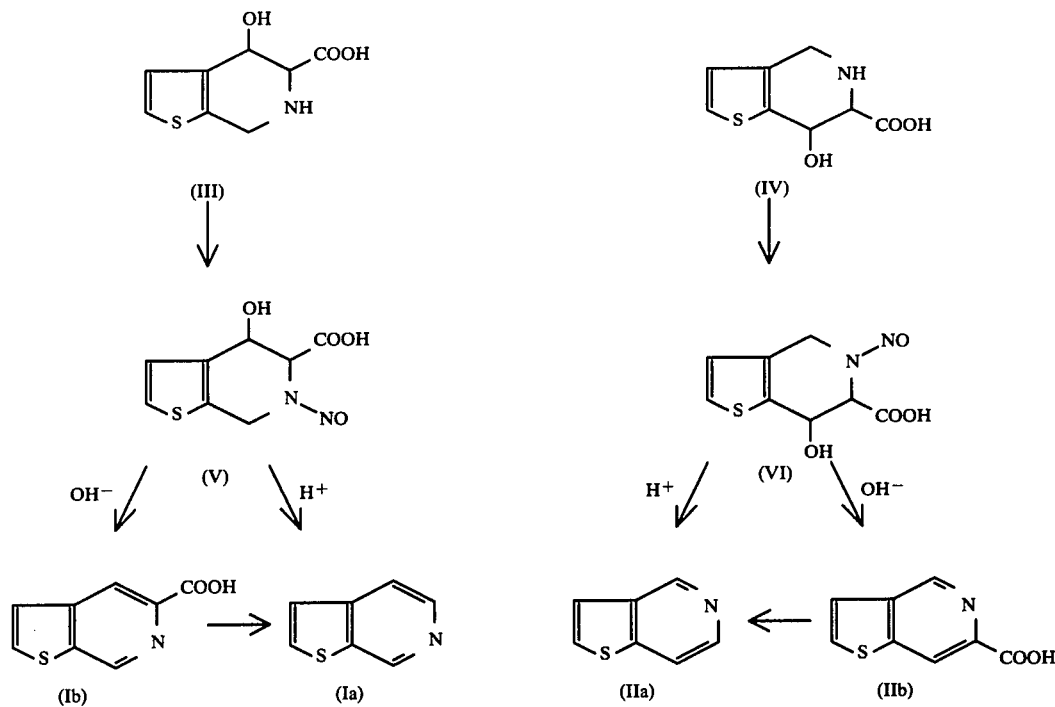

The starting compounds of the formula (III) or (IV) may be prepared by reaction of a compound of the formula (VII) (VIII)

with an aqueous formaldehyde solution, in the presence of a strong acid.

The serines of the formula (VII) or (VIII) may be obtained in the following manner:
- -β-(2-thienyl)serine may be prepared according to the method disclosed by G. Weitnauer, Gazz. Chim. Ital., 1951, 81, 162;
- -β-(3-thienyl)serine may be prepared from 3-thienaldehyde, according to the above Weitnauer process. Hydrochloride: white crystals, M.p.=241° C.

The following non-limiting Examples are given to illustrate the present invention.

EXAMPLE 1

Preparation of 5-carboxy-4-hydroxy-6-nitroso-4,5,6,7-tetrahydro-thieno[2,3-c]pyridine To a magnetically stirred suspension of 20 g (0.1 mole) 5-carboxy-4-hydroxy-4,5,6,7-tetrahydro-thieno[2,3-c]pyridine in 200 cc 3 N hydrochloric acid maintained at 10° C. is added dropwise a 10% aqueous sodium nitrite solution (200 cc; 2.9 equivalents) and the resulting mixture is stirred at room temperature for 3 hours. The reaction medium remains heterogeneous throughout this step and nitrous fumes are evolved. The resulting precipitate is filtered off, washed with water and dried in vacuo, to give beige crystals (paste melting from 100° C.) in a yield of 21.3 g (93%).

EXAMPLE 2

The procedure of Example 1 gives 6-carboxy-7-hydroxy-5-nitroso-4,5,6,7-tetrahydro-thieno[3,2-c]pyridine. The product melts as a paste from 60° C. Yield: 97%.

EXAMPLE 3

Preparation of thieno[3,2-c]pyridine

A solution of 24 g of the nitroso derivative obtained in Example 2 in 200 cc 6 N hydrochlorid acid is heated at 60° C. for 2 hours. Gas is evolved, and russet fumes are formed. After cooling, the brown reaction medium is made basic with aqueous sodium hydroxide and is then extracted with methylene chloride. The organic extracts are washed with water, dried over sodium sulfate, decolorized with carbon black, filtered through talc and evaporated to dryness. Vacuum distillation of the residue gives 6.5 g (overall yield, from the starting material of the formula (IV): 43%) thieno[3,2-c]pyridine which crystallizes on cooling. M.p. <50° C.

EXAMPLE 4

The procedure of Example 3, starting from the nitroso compound obtained in Example 1, gives thieno[2,3-c]pyridine; M.p. <50° C. Yield: 47%.

EXAMPLE 5

Preparation of 5-carboxy-thieno[2,3-c]pyridine

An initially homogeneous solution of 10 g (0.044 mole) of the nitroso derivative obtained in Example 1, 20 cc ethanol and 60 cc aqueous 20% sodium hydroxide is refluxed for 2 hours. After cooling and addition of ethanol, the resulting precipitate is filtered off, washed with ethanol and then with ether, after which it is dried. The resulting sodium salt (M.p.=260° C.; 4.7 g; 60%) is treated with 23 cc (1 equivalent) N hydrochloric acid. The material is found to dissolve at first and then to reprecipitate. It is directly recrystallized after addition of 27 cc water, to give 2.5 g (32%) pink crystals, M.p.=246° C.

EXAMPLE 6

Starting from the nitroso derivative of Example 2, the procedure of Example 5 gives 6-carboxy-thieno[3,2-c]pyridine. Pink crystals. M.p.=212° C. Yield: 84%.

EXAMPLE 7

Preparation of thieno[3,2-c]pyridine 11.4 g of the derivative of the formula (IV) of Example 2 is added portionwise to 55 cc trifluoroacetic acid stirred at room temperature. The temperature rises from 19° C. to 24° C., and russet fumes are evolved. The material is allowed to cool to room temperature; the reaction mixture is then poured over ice, made basic by addition of concentrated aqueous ammonia and extracted with diisopropyl ether. The organic extracts are washed with water, dried over sodium sulfate and evaporated to dryness. Distillation in vacuo of the residue gives 3.8 g (Yield: 56%) thieno[3,2-c]pyridine.

Having now described my invention what I claim as new and desire to secure by Letters Patent is:

1. Process for the preparation of a compound selected from the compounds having the formulae

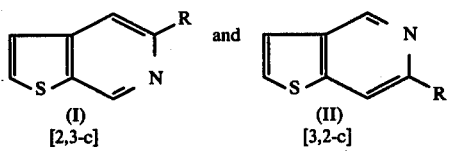

wherein R is selected from hydrogen and carboxy, comprising adding an aqueous solution of an alkali metal nitrite to an acidic solution of a compound selected from the compounds having the formulae

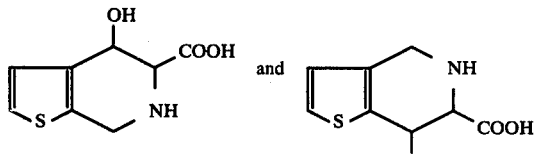

to give, respectively, a compound of formulae

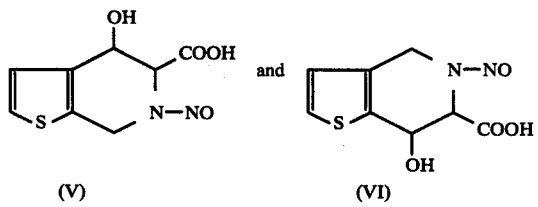

and then reacting a compound of formula (V) or (VI) respectively with an acid selected from hydrochloric acid, hydrobromic acid, sulfuric acid and trifluoroacetic acid and making the reaction mixture basic with an alkali metal hydroxide, to give the derivatives of formula (I) and (II) respectively, in which R is hydrogen, or reacting said compound (V) or (VI) with an alkali metal hydroxide in aqueous solution at the reflux temperature and subsequent neutralization, to give the derivatives of the formula (I) and (II), respectively, in which R is carboxy.

* * * * *